US010551336B2

(12) United States Patent
Chang et al.

(10) Patent No.: US 10,551,336 B2
(45) Date of Patent: Feb. 4, 2020

(54) SENSING DEVICE FOR MEASURING A LEVEL OF AN ANALYTE, METHOD OF FABRICATION THEREOF

(71) Applicant: Agency for Science, Technology and Research, Singapore (SG)

(72) Inventors: Kok Leong Chang, Singapore (SG); Zi En Ooi, Singapore (SG); Jie Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 145 days.

(21) Appl. No.: 15/577,266

(22) PCT Filed: May 30, 2016

(86) PCT No.: PCT/SG2016/050256
§ 371 (c)(1),
(2) Date: Nov. 27, 2017

(87) PCT Pub. No.: WO2016/190820
PCT Pub. Date: Dec. 1, 2016

(65) Prior Publication Data
US 2018/0149608 A1 May 31, 2018

(30) Foreign Application Priority Data
May 28, 2015 (SG) .......................... 10201504195W

(51) Int. Cl.
*G01R 31/00* (2006.01)
*G01N 27/12* (2006.01)
*G01N 27/416* (2006.01)

(52) U.S. Cl.
CPC ....... *G01N 27/122* (2013.01); *G01N 27/4167* (2013.01)

(58) Field of Classification Search
USPC ......... 324/691–693, 696, 699, 71.1; 73/1.31, 73/1.73, 53.04, 304 R
See application file for complete search history.

(56) References Cited

U.S. PATENT DOCUMENTS 4,112,356 A  9/1978 Toy
4,235,096 A  11/1980 Yasuda et al.
(Continued)

FOREIGN PATENT DOCUMENTS

WO  2012125494 A2  9/2012
WO  2015033229 A2  3/2015

OTHER PUBLICATIONS

International Preliminary Report on Patentability for International Application No. PCT/SG2016/050256 dated Aug. 1 2017, pp. 1-18.
(Continued)

*Primary Examiner* — Vincent Q Nguyen
(74) *Attorney, Agent, or Firm* — Winstead PC

(57) ABSTRACT

There is provided a sensing device for measuring a level of an analyte. The sensing device includes a sensing element configured to sense the analyte and produce an electrical output which is variable based on the level of the analyte sensed, a measurement circuit including a reference element for providing an electrical property, the measurement circuit being connected to the sensing element and configured to provide a measurement output signal based on the electrical property of the reference element and the electrical output of the sensing element, whereby the measurement output signal indicates the level of the analyte sensed with respect to the electrical property of the reference element. There is also provided a corresponding method of fabricating the sensing device.

18 Claims, 10 Drawing Sheets

(56) References Cited

U.S. PATENT DOCUMENTS

| | | | |
|---|---|---|---|
| 4,324,218 A | | 4/1982 | Hattori et al. |
| 5,027,077 A | | 6/1991 | Yanagisawa et al. |
| 5,315,673 A | | 5/1994 | Stetter et al. |
| 5,400,643 A | | 3/1995 | De Angelis et al. |
| 5,616,850 A | | 4/1997 | Sage |
| 6,242,891 B1 | * | 6/2001 | Parsonage ........ G01R 19/16542 320/132 |
| 8,614,572 B2 | | 12/2013 | Florescu et al. |
| 8,623,283 B2 | | 1/2014 | Van Breemen et al. |
| 2008/0156091 A1 | * | 7/2008 | Hickman .............. G01F 23/246 73/304 R |
| 2009/0266442 A1 | * | 10/2009 | Duscher ................ G01F 23/243 141/95 |
| 2012/0011931 A1 | * | 1/2012 | Ichisawa ................. G01F 23/38 73/317 |
| 2012/0270205 A1 | | 10/2012 | Patel et al. |
| 2014/0377879 A1 | | 12/2014 | Sharrock et al. |

OTHER PUBLICATIONS

Written Opinion of the International Searching Authority for International Application No. PCT/SG2016/050256 dated Jul. 25, 2016, pp. 1-5.

* cited by examiner

SENSING DEVICE FOR MEASURING A LEVEL OF AN ANALYTE, METHOD OF FABRICATION THEREOF

CROSS-REFERENCE TO RELATED APPLICATION

This application claims the benefit of priority of Singapore Patent Application No. 10201504195 W, filed 28 May 2015, the content of which being hereby incorporated by reference in its entirety for all purposes.

TECHNICAL FIELD

The present invention generally relates to a sensing device for measuring a level of an analyte, and a method of fabricating the sensing device.

BACKGROUND

Sensors are usually either optical or electronic. Conventional optical sensors rely on materials that change colour according to analyte levels. This is an economical approach for measuring coarse analyte levels, but with the need for higher resolution, colour differentiation between fine analyte levels becomes challenging. To obtain higher resolution sensing, conventional electronic sensors usually measure the generated electrochemical potential or physical electrical signals. However, such conventional electronic sensors would require a high input impedance circuit for signal acquisition because the electrical signal generated is usually very low (e.g., less than 100 mV). Therefore, such conventional electronic sensors have been found to require a sensor front-end and a signal measurement/processing back-end. The front-end can be made low-cost by printing sensor materials on paper or plastic. However, the back-end signal measurement/acquisition circuits, due to their need to measure very low voltages, are nevertheless based on traditional electronics. Therefore, although such conventional electronic sensors may yield a low-cost front-end sensor, they still require a relatively expensive back-end signal measurement and display device. As a result, the need for a back-end signal measurement/acquisition device in such conventional electronic sensors renders high resolution sensing still relatively expensive for low-cost applications.

A need therefore exists to provide a sensing device for measuring a level of an analyte, and a method of fabrication thereof, that seek to address or at least ameliorate one or more of the problems associated with conventional electronic sensors. It is against this background that the present invention has been developed.

SUMMARY

According to a first aspect of the present invention, there is provided a sensing device for measuring a level of an analyte, the sensing device comprising:

a sensing element configured to sense the analyte and produce an electrical output which is variable based on the level of the analyte sensed;

a measurement circuit comprising a reference element for providing an electrical property, the measurement circuit being connected to the sensing element and configured to provide a measurement output signal based on the electrical property of the reference element and the electrical output of the sensing element, wherein the measurement output signal indicates the level of the analyte sensed with respect to the electrical property of the reference element.

In various embodiments, the measurement circuit further comprises a power source for providing a supply voltage, the measurement output signal is an output voltage signal, and the measurement circuit is configured such that a maximum range of the output voltage signal is proportional to the supply voltage of the power source.

In various embodiments, the maximum range of the output voltage signal is substantially the same as the supply voltage or proportionally greater than the supply voltage.

In various embodiments, the sensing element comprises a conductive member and a sensing material disposed on the conductive member for receiving the analyte, the sensing material having an electrical property which is variable based on the level of the analyte received, thereby causing the electrical output of the sensing element at the conductive member to be variable based on the level of the analyte sensed.

In various embodiments, the conductive member comprises a plurality of spaced apart electrodes, the sensing material being disposed on the plurality of spaced apart electrodes so as to provide an electrical connection between the spaced apart electrodes via the sensing material.

In various embodiments, the sensing element and the measurement circuit are integrally formed on a substrate.

In various embodiments, the sensing element and the measurement circuit are printed on the substrate.

In various embodiments, the electrical property is an electrical conductivity of the sensing material, and the electrical output of the sensing element at the conductive member corresponds to the electrical conductivity of the sensing material.

In various embodiments, the reference element comprises a resistor, and the electrical property of the reference element is a predetermined electrical resistance corresponding to a reference level of the analyte such that the measurement output signal indicates the level of the analyte sensed with respect to the reference level of the analyte based on the electrical output of the sensing element with respect to the predetermined electrical resistance of the reference element.

In various embodiments, the sensing device further comprises one or more additional sensing elements and one or more additional reference elements, each additional sensing element configured to sense the analyte and produce an electrical output which is variable based the level of the analyte sensed, and each additional reference element comprising a resistor, and the electrical property of the reference element is a predetermined electrical resistance corresponding to an additional reference level of the analyte for measuring the level of the analyte sensed with respect to the predetermined electrical resistance of the additional reference element.

In various embodiments, the reference element is a second sensing element, the second sensing element configured to sense the analyte or another analyte and produce an electrical output which is variable based the level of the analyte or said another analyte sensed.

In various embodiments, the sensing element and the reference element are connected in series, and the measurement output signal is output from an output node located between the sensing element and the reference element.

In various embodiments, the measurement circuit is further configured to incorporate a differential amplifier to provide additional amplification to the measurement output signal.

According to a second aspect of the present invention, there is provided a method of fabricating a sensing device for measuring a level of an analyte, the method comprising:

forming a sensing element configured to sense the analyte and produce an electrical output which is variable based on the level of the analyte sensed;

forming a measurement circuit comprising a reference element for providing an electrical property, the measurement circuit being connected to the sensing element and configured to provide a measurement output signal based on the electrical property of the reference element and the electrical output of the sensing element, wherein the measurement output signal indicates the level of the analyte sensed with respect to the electrical property of the reference element.

In various embodiments, the measurement circuit further comprises a power source for providing a supply voltage, the measurement output signal is an output voltage signal, and the measurement circuit is configured such that a maximum range of the output voltage signal is proportional to the supply voltage of the power source.

In various embodiments, forming a sensing element comprises forming a conductive member and forming a sensing material disposed on the conductive member for receiving the analyte, the sensing material having an electrical property which is variable based on the level of the analyte received, thereby causing the electrical output of the sensing element at the conductive member to be variable based on the level of the analyte sensed.

In various embodiments, the sensing element and the measurement circuit are integrally formed on a substrate.

In various embodiments, the sensing element and the measurement circuit are printed on the substrate.

In various embodiments, the electrical property is an electrical conductivity of the sensing material, and the electrical output of the sensing element at the conductive member corresponds to the electrical conductivity of the sensing material.

In various embodiments, the sensing element and the reference element are connected in series, and the measurement output signal is output from an output node located between the sensing element and the reference element.

BRIEF DESCRIPTION OF THE DRAWINGS

Embodiments of the present invention will be better understood and readily apparent to one of ordinary skill in the art from the following written description, by way of example only, and in conjunction with the drawings, in which.

DETAILED DESCRIPTION

Various embodiments of the present invention provide a sensing device for measuring/detecting a level of an analyte, and a method of fabrication the sensing device. For example and without limitations, the sensing device may be applied to sense/detect analytes from various mediums/sensing sources (including a combination thereof), such as environmental changes (e.g., temperature, humidity, etc.), chemical species (e.g., solid, liquid or gas) or biological triggers (e.g., pH, etc.). It will be appreciated to a person skilled in the art that measuring/detecting a level of an analyte includes detecting/sensing the presence of the analyte, that is, simply detecting/sensing whether the analyte is present or not.

As discussed in the background of the present specification, conventional low-cost sensors have been found to be either rudimentary which do not sufficiently or unambiguously indicate source/analyte levels (e.g., colour change in litmus paper are vulnerable to perception) or actually only partly low-cost (e.g., a low-cost front-end sensor but a relatively expensive and separate back-end signal measurement device is required due to low-voltage measurement requirements, such as a low-voltage amplifier circuit in a separate signal reader in e.g., glucose sensors). Therefore, although conventional electronic sensors may allow the front-end sensing to be printed, the back-end sensing is not able to be printed due to low-voltage measurement requirements and is instead realized based on traditional electronics. In contrast, various embodiments of the present invention enable both the front-end sensing and back-end signal measurement/acquisition circuits to be printed on a substrate. In this regard, being able to print both the front-end sensing and back-end signal measurement circuits are highly advantageously as they can be integrated onto one (i.e., a single) substrate (e.g., a flexible substrate) without requiring a separate and relatively expensive back-end signal measurement device, thereby significantly reducing costs and complexity as well as enabling low-cost applications.

Figure 1:
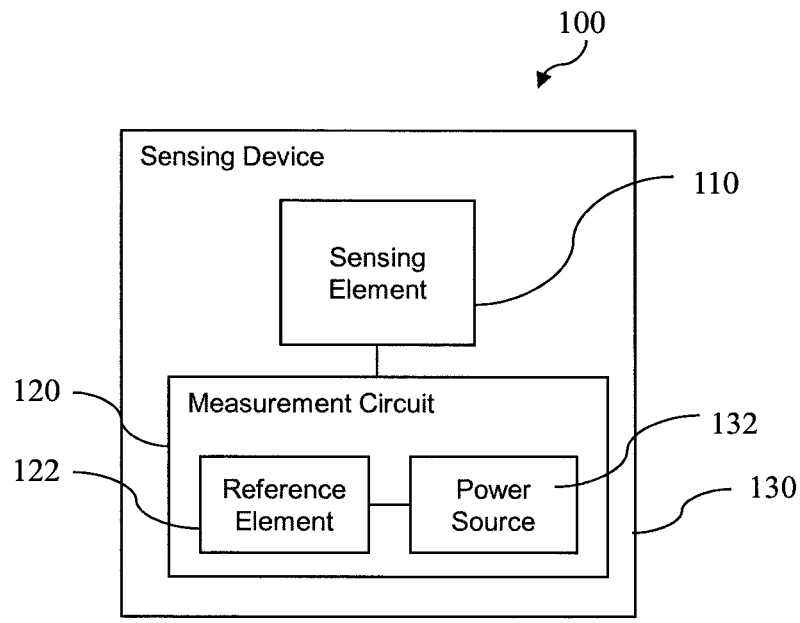
FIG. 1 depicts a sensing device for measuring/detecting a level of an analyte according to various embodiments of the present invention.

FIG. 1 depicts a sensing device 100 for measuring/detecting a level of an analyte according to various embodiments of the present invention. The sensing device 100 comprises a sensing element 110 configured to sense/detect the analyte and produce an electrical output which is variable based on the level of the analyte sensed/detected, and a measurement circuit 120 comprising a reference element 122 for providing an electrical property. The measurement circuit 120 is electrically connected to the sensing element 110 and configured to provide a measurement output signal based on the electrical property of the reference element 122 and the electrical output of the sensing element 110, whereby the measurement output signal indicates the level of the analyte sensed/detected with respect to the electrical property of the reference element 122.

For example, providing a measurement circuit 120 including a reference element 122 advantageously enables the sensing device 100 to measure the analyte level by comparing the electrical output of the sensing element 110 (which is variable based on the analyte level sensed) with a predetermined/reference electrical property (e.g., resistance/conductivity value) of the reference element 122 corresponding to (associated with) a reference level of the analyte. Therefore, the analyte level sensed can be measured with respect to the reference element 122, in contrast with measuring the analyte level directly/entirely from the electrical signal generated by the sensing element sensing the analyte (which would require a high input impedance circuit for signal measurement/acquisition due to the electrical signal generated being very low (e.g., less than 100 mV) as explained hereinbefore). Accordingly, since conventional high impedance circuits are not required, the measurement circuit 120 according to various embodiments of the present invention can advantageously be integrally formed with the sensing element 110 on a substrate (e.g., a single substrate) 130. That is, the sensing element 110 forms part of the measurement circuit 120 for signal measurement/acquisition as an integrated circuit. Furthermore, as a result, both the sensing element 110 and the measurement circuit 120 may be printed on a substrate 130, thereby significantly reducing costs and complexity and enabling low-cost applications.

In various embodiments, the sensing device 100 further comprises a power source 132 for providing a supply/driving voltage to the sensing element 110 and the reference element 122, and the measurement output signal is an output voltage signal. Furthermore, the measurement circuit 120 is configured such that a maximum range of the output voltage signal is proportional to the supply voltage of the power source 132. In various embodiments, the maximum range of the output voltage signal is substantially the same as the supply voltage or proportionally greater than the supply voltage. For example and without limitation, in the case of the supply/driving voltage being +/−10V, the maximum range of the output voltage may also be +/−10V or proportionally greater such as +/−20V (e.g., by configuring the measurement circuit 120 to have additional amplification such as by incorporating a differential amplifier, which will be described later below). Such a configuration of the measurement circuit 120 advantageously enables the measurement output signal level to be controlled based on the supply voltage (i.e., proportional to the supply voltage). As a result, the measurement output signal level can be increased/improved based on the supply voltage to avoid requiring low-voltage signal processing (which would require, e.g., a relatively expensive low-voltage amplifier circuit in a separate signal reader). Accordingly, as the measurement circuit 120 is able to provide sufficient measurement output signal level without requiring high impedance circuits, the measurement circuit 120 can advantageously be integrally formed with the sensing element 110 on a substrate 130.

In various embodiments, the electrical output of the sensing element 110 corresponds to its electrical conductivity in the measurement circuit 120. That is, the sensing element 110 is configured to sense the analyte based on electrical conductivity changes as a result of the level of analyte sensed. In this regard, since the variable parameter for sensing/detecting analyte is the electrical conductivity of the sensing element 110, the measurement output signal (e.g., output voltage signal) of the measurement circuit 120 would correspondingly change with the electrical conductivity of the sensing element 110, thus enabling the measurement of the level of the analyte to be performed with high sensitivity for high resolution sensing. For example, the sensitivity of the sensing element 110 (changes in electrical conductivity) can be configured by selecting appropriate sensing materials for sensing the analyte for various purposes. For example, specific sensing materials may be selected for sensing specific analytes. Furthermore, as the sensing element 110 is electrically connected to the power source 132 (with the measurement circuit 120 being configured such that the measurement output signal (output voltage signal) is proportional to the supply voltage of the power source 132), changes in electrical conductivity based on the level of the analyte sensed would be translated into a change in the output voltage signal (with respect to the reference element 122) at a signal level proportional to the supply voltage, thus advantageously enabling voltage readout at a sufficient signal level without requiring low-voltage signal processing.

Figure 2:
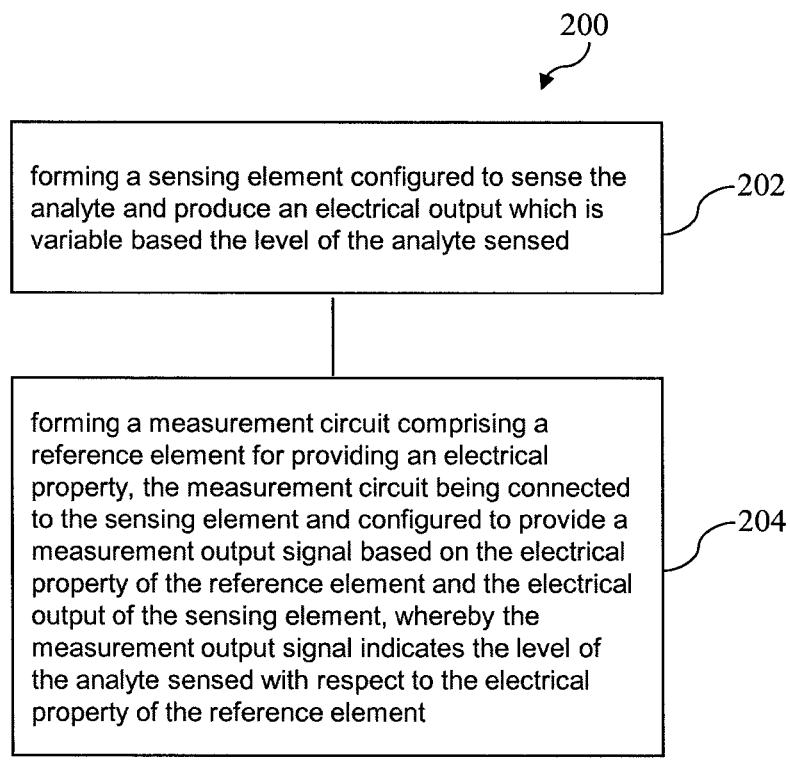
FIG. 2 depicts a flow diagram of a method of fabricating a sensing device for measuring a level of an analyte according to various embodiments of the present invention.

FIG. 2 depicts a flow diagram of a method 200 of fabricating a sensing device for measuring a level of an analyte according to various embodiments of the present invention. The method 200 comprises a step 202 of forming a sensing element 110 configured to sense the analyte and produce an electrical output which is variable based the level of the analyte sensed, and a step 204 of forming a measurement circuit 120 comprising a reference element 122 for providing an electrical property, the measurement circuit 120 being connected to the sensing element 110 and configured to provide a measurement output signal based on the electrical property of the reference element 122 and the electrical output of the sensing element 110, whereby the measurement output signal indicates the level of the analyte sensed with respect to the electrical property of the reference element 122.

It will be appreciated to a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In order that the present invention may be readily understood and put into practical effect, various example embodiments of the present inventions will be described hereinafter by way of examples only and not limitations. It will be appreciated by a person skilled in the art that the present invention may, however, be embodied in various different forms and should not be construed as limited to the example embodiments set forth hereinafter. Rather, these example embodiments are provided so that this disclosure will be thorough and complete, and will fully convey the scope of the present invention to those skilled in the art.

Figure 3A:
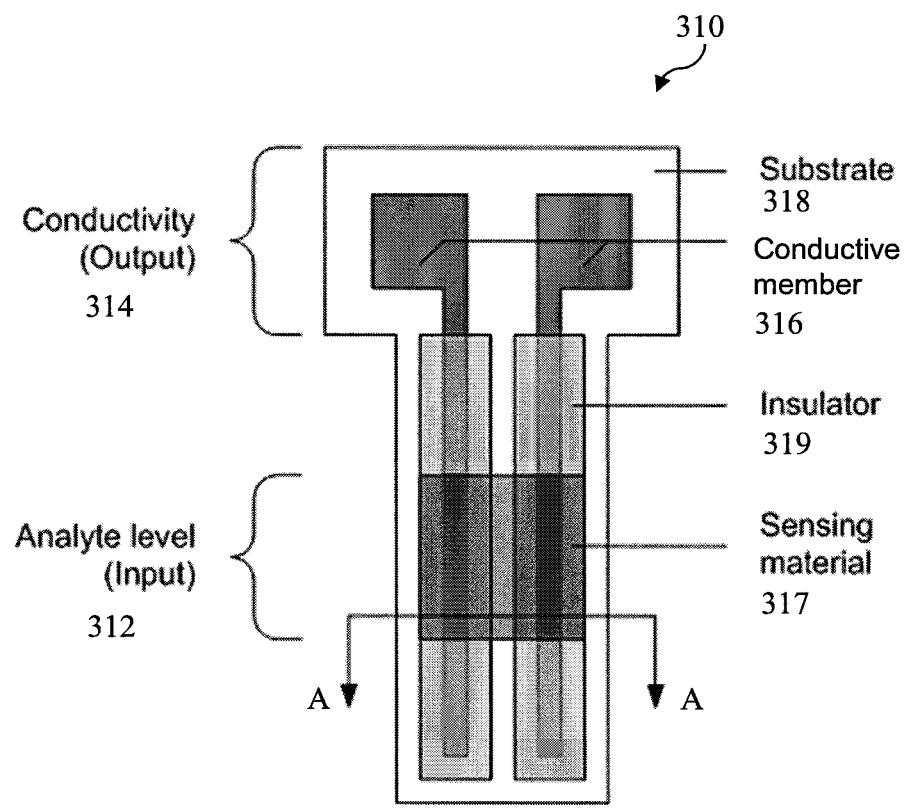
FIG. 3A depicts a schematic drawing of a sensing element according to various example embodiments of the present invention.
Figure 3B:
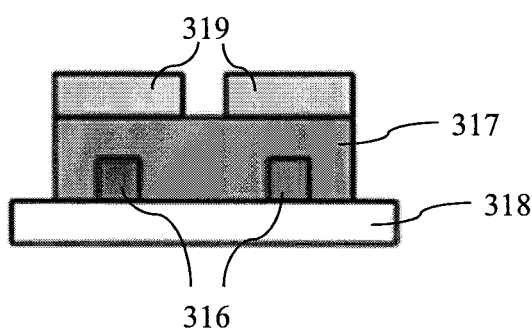
FIG. 3B depicts a schematic drawing of a cross-sectional view of the sensing element along line A-A of FIG. 3A.

FIG. 3A depicts a schematic drawing of a sensing element 310 according to various example embodiments of the present invention configured to sense/detect the analyte 312 and produce an electrical output 314 which is variable based on the level of the analyte sensed/detected. FIG. 3B depicts a schematic drawing of a cross-sectional view of the sensing element 310 along line A-A of FIG. 3A. As shown in FIGS. 3A and 3B, the sensing element 310 comprises a conductive member 316 and a sensing material 317 disposed on the conductive member 316 for receiving the analyte 312. In particular, the sensing material 317 has an electrical property which is variable based on the level of the analyte 312 received (e.g., detected or in contact therewith), thereby causing the electrical output 314 of the sensing element 310 at the conductive member 316 to be variable based on the level of the analyte 312 sensed.

In the example embodiment of FIGS. 3A and 3B, the conductive member 316 comprises a plurality of spaced apart electrodes (e.g., two spaced apart electrodes shown in FIGS. 3A and 3B as an example illustration only). The sensing material 317 is disposed on the plurality of spaced apart electrodes 316 so as to provide an electrical connection between the spaced apart electrodes 316 via the sensing material 317. In particular, since the electrodes 316 are spaced apart, the sensing material 317 is provided on the two electrodes 316 to bridge the gap therebetween so as to provide an electrical conduction path between the electrodes via the sensing material 317. As a result, the electrical output 314 of the sensing element 310 is based on or corresponds to the electrical property (electrical conductivity) of the sensing material 317. As shown in FIG. 3B, the electrodes 316 may be disposed on a substrate 318 and the sensing material 317 may then be disposed over the electrodes 316 so as to encapsulate the electrodes 316 on the substrate 318. In various other embodiments (not shown), the sensing material 317 may be disposed on the substrate 318 (including under and over the electrodes 316) so as to completely encapsulate the electrodes 316 cross-sectionally. It will be appreciated to a person skilled in the art that the present invention is not limited to any particular sensing material 317 as long as the sensing material has an electrical property which is variable based on the level of the analyte received. It will also be appreciated to a person skilled in the art that specific sensing materials may be selected for detecting/sensing specific analytes for various sensing applications. By way of examples only and without limitations, the sensing material may be made of one or more of thermoelectric polymer (conductive polymers), pyroelectrical materials (PVDF), semiconducting thermocouple materials, thermoelectric composite (polymer and carbon nanotube or SiGe), and so on, for temperature sensors, polypyrrole, poly(anilinesulfonic acid), and so on, for humidity sensors, and polypyrrole, polyaniline (PANI), polythiophene, metal oxides (e.g., ZnO), and so on, for biosensors.

In various example embodiments, the conductive member 316 may be insulated so as to avoid being exposed to the analyte 312. For example, as illustrated in FIGS. 3A and 3B, an insulating layer 319 may be disposed over and along each of the electrodes 316, including over portions of the sensing material 317 above the respective electrodes 316. As a result, when sensing analyte, the analyte 312 will only come into contact with the sensing material 317 (e.g., the exposed portion of the sensing material as shown in FIGS. 3A and 3B) but not the electrodes 316.

Figure 4:
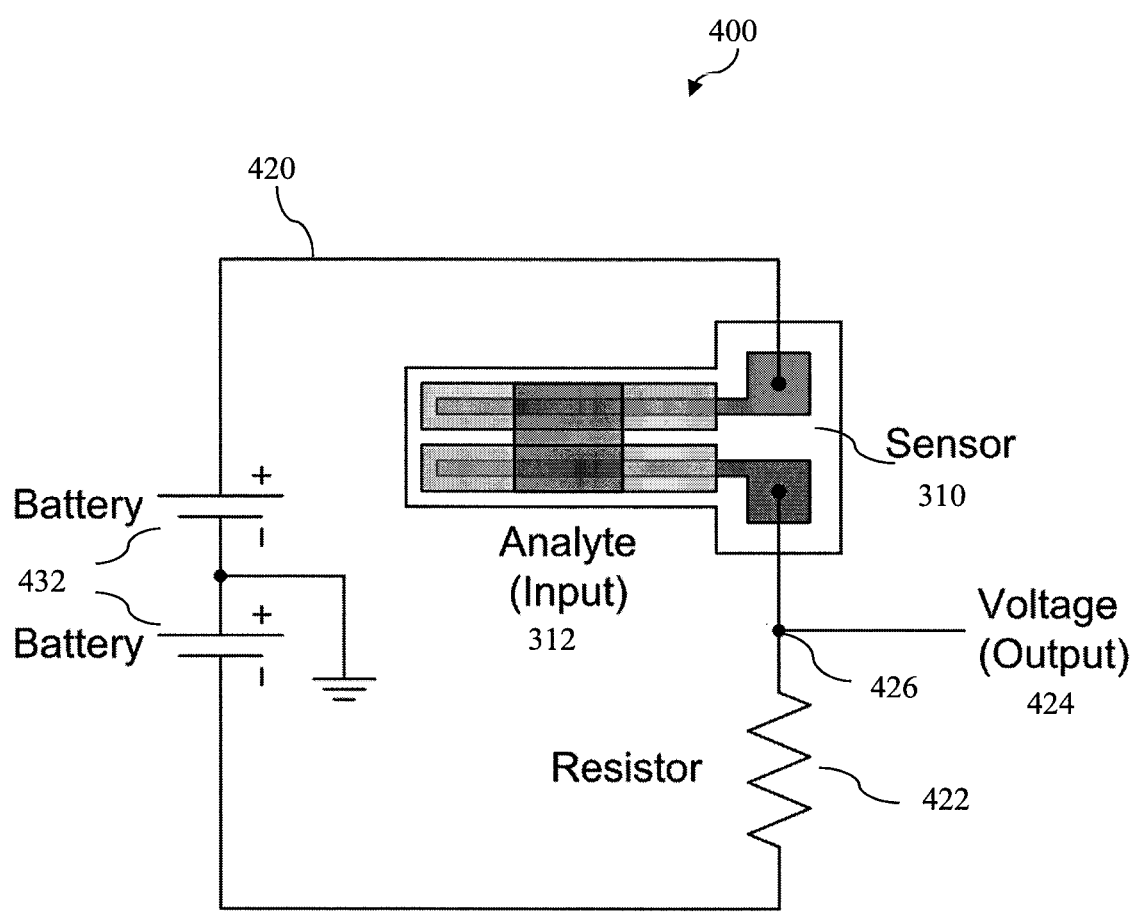
FIG. 4 depicts a schematic circuit drawing of a sensing device for measuring/detecting a level of an analyte according to various example embodiments of the present invention.

FIG. 4 depicts a schematic circuit drawing of a sensing device 400 for measuring/detecting a level of an analyte according to various example embodiments of the present invention. The sensing device 400 comprises the sensing element 310 as described above with reference to FIGS. 3A and 3B and a measurement circuit 420 comprising a reference element 422 for providing an electrical property. As shown in FIG. 4, the measurement circuit 420 is connected to the sensing element 310 and configured to provide a measurement output signal 424 based on the electrical property of the reference element 422 and the electrical output of the sensing element 310, whereby the measurement output signal 424 indicates the level of the analyte 312 sensed with respect to the electrical property of the reference element 422.

In the example embodiment of FIG. 4 as shown, the power source 432 provides a supply/driving voltage, and the measurement output signal 424 is an output voltage signal. It can be appreciated by a person skilled in the art that the configuration of the measurement circuit 420 is such that a maximum range of the output voltage signal is proportional to the supply voltage of the power source 432. Furthermore, in the example embodiment of FIG. 4 as shown, the reference element 422 comprises a resistor, and the power source 432 comprises two batteries connected in series. In this regard, the electrical property of the reference element 422 is a predetermined electrical resistance corresponding to (associated with) a reference level of the analyte such that the measurement output signal 424 indicates the level of the analyte sensed with respect to the reference level of the analyte based on the electrical output of the sensing element 310 with respect to the predetermined electrical resistance of the reference element 422. Accordingly, a change in the electrical conductivity of the sensing element 310 when sensing analyte 312 is translated into a change in the output voltage signal 424, thereby enabling the measurement of the level of the analyte 312 with respect to the electrical property of the reference element 422.

In the example embodiment of FIG. 4, the sensing element 310 and the reference element 422 are connected in series, and the measurement output signal 424 is output from an output node 426 located between the sensing element 310 and the reference element 422. In particular, in the example embodiment of FIG. 4, the measurement circuit 420 is configured with the sensing element 310 and the reference element 422 (connected in series) connected to the power source 432 such that the sensing element 310 is connected between a first terminal (e.g., a positive terminal) of the power source 432 and the output node 426, and the reference element 422 is connected between a second terminal (e.g., a negative terminal) of the power source and the output node 426. In the example embodiment, as shown, a ground is applied in between the two batteries 432 connected in series, which functions as a voltage divider for changing the porosity of the output voltage signal 424 so as to, e.g., drive the bi-stable and/or electrochromic display. Accordingly, the measurement output signal (output voltage signal) 424 will indicate the electrical conductivity of the sensing element 310, and thus the analyte level sensed with respect to the reference level of the analyte provided by the reference element 422.

For example and in general, according to the measurement circuit 420 as shown in FIG. 4, the output voltage signal 424 will be greater than 0V if the electrical conductivity of the sensing element 310 is greater than that of the reference element 422. On the other hand, the output voltage signal 424 will be below 0V if electrical conductivity of the sensing element 310 is less than that of the reference element 422. In addition, the output voltage signal 424 will be 0V when the electrical conductivities of the sensing element 310 and the reference element 422 are identical. Accordingly, the measurement circuit 420 can be used to indicate the analyte level sensed compared to a predetermined/reference analyte level (preset by the electrical resistance of the reference element 422). For example, when the output voltage signal 424 is 0V, this indicates that the analyte level sensed by is at the predetermined analyte level. On the other hand, the analyte level sensed is either above or below the predetermined analyte level if the output voltage is not at 0V (i.e., above or below 0V). In various embodiments, the amount in which the output voltage signal 424 is above or below a predetermined voltage level (e.g., 0V) provides an indication (e.g., proportionally) of the analyte level above or below the predetermined reference analyte level. That is, the analyte level can be determined with respect to the predetermined reference analyte level based on the amount of the output voltage signal 424 is above or below the predetermined voltage level. It will be appreciated that the relationship between the amount output voltage signal above or below the predetermined voltage level and the corresponding analyte level above or below the predetermined reference analyte level depends on the electrical property (e.g., sensitivity in electrical conductivity changes) of the sensing material 317, and appropriate/suitable sensing material 317 may be used/selected in the sensing element 310 for various purposes/applications. For example, if a sensing material 317 is capable of sensing a desired resolution, the measurement circuit 420 may be configured/tuned to readout the changes in electrical property provided by the sensing element 310 by balancing/configuring the sensing element output and the reference element output accordingly.

The above configuration of the measurement circuit 420 yields output voltage signal levels proportional to the power source 432 and thus the output voltage signal levels are significantly higher compared to the conventional electronic sensors as discussed hereinbefore. Advantageously, since the output voltage signal levels are much higher, traditional high impedance circuits are not required according to various embodiments of the present invention. Accordingly, the measurement circuit 120 can advantageously be integrally formed with the sensing element 110 on a substrate 130/318. That is, the sensing element 110 forms part of the measurement circuit 120 for signal measurement/acquisition as an integrated circuit, whereas conventional electronic sensors require separate sensor and signal measurement/acquisition circuit (with high input impedance circuit) as explained hereinbefore. As a result, both the sensing element 110 and the measurement circuit 120 may be printed on a substrate 130/318, thereby significantly reducing costs and complexity and enabling low-cost applications.

Figure 5A:
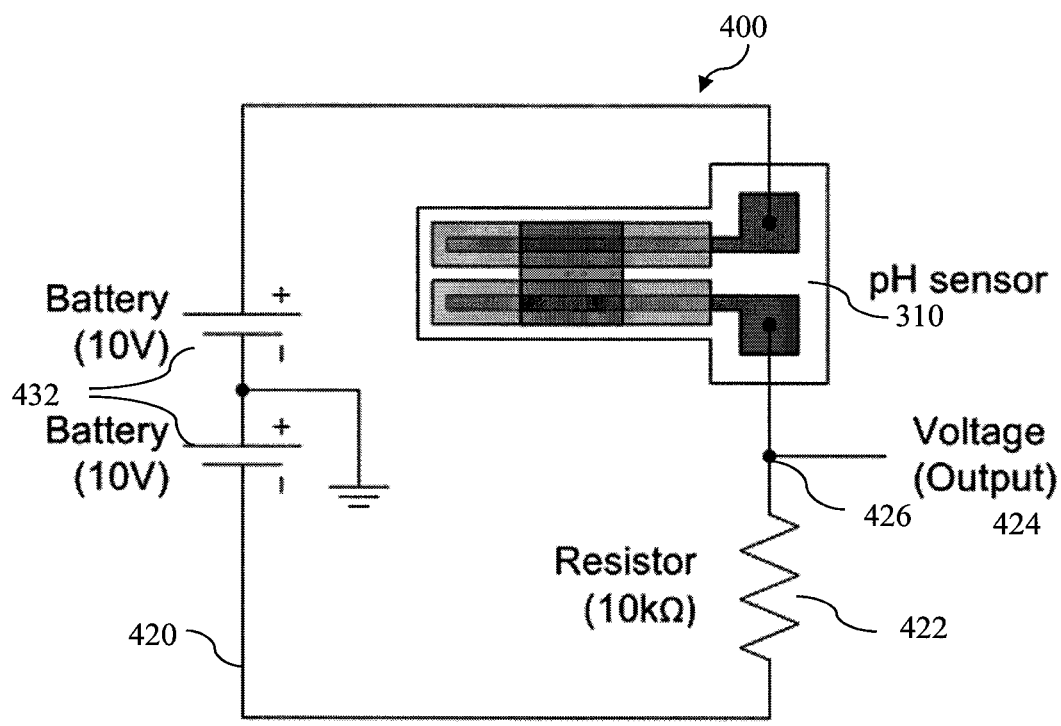
FIG. 5A depicts a schematic circuit drawing of the sensing device implemented or used as a pH sensor device according to an example embodiment of the present invention.
Figure 5B:
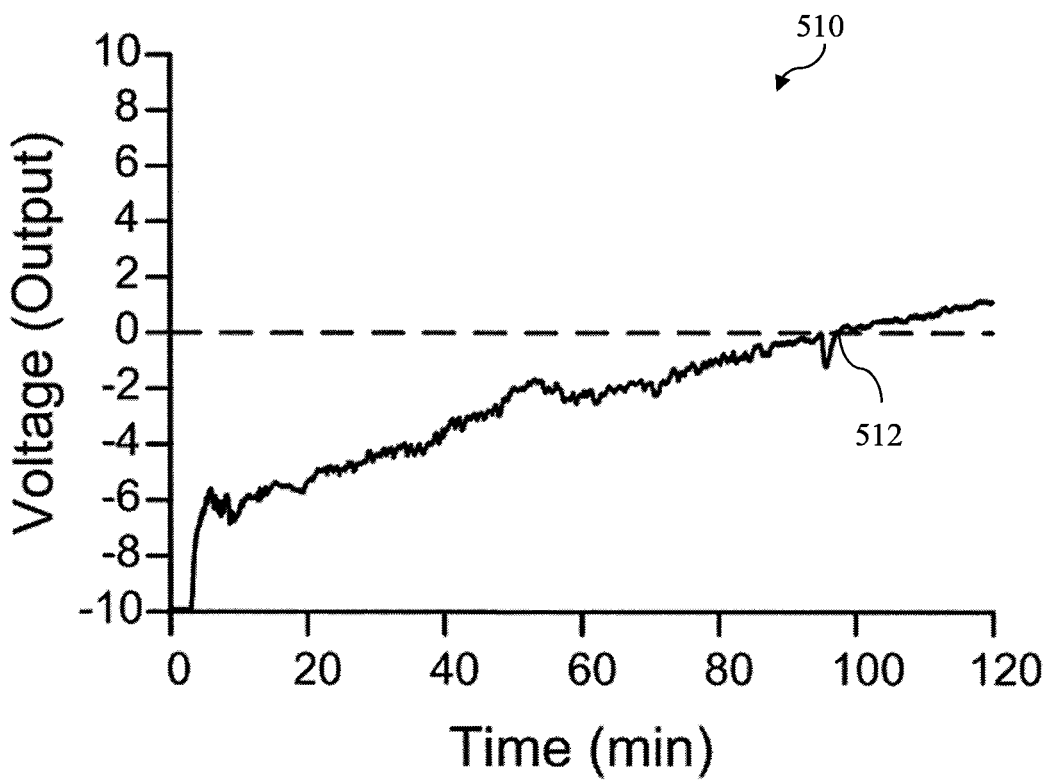
FIG. 5B depicts a plot of the output voltage signal (V) over time (minutes) of the pH sensor device of FIG. 5A.

As an example, FIG. 5A depicts a schematic circuit drawing of the sensing device 400 implemented or used as a pH sensor device. The measurement circuit 420 in the example comprises a power source including two 10V batteries 432 and a reference element 422 including a resistor with a resistance value of 10 kΩ. FIG. 5B depicts a plot 510 of the output voltage signal (V) 424 over time (minutes). From the plot 510, it can be observed that as the pH reduces with time, the resistance of the sensing element 310 decreases (i.e., electrical conductivity increases) and thus increasing the voltage across the resistor 422. At approximately 100 minutes, the output voltage signal 424 crosses 0V indicating that the resistance of the sensing element 310 (being used as a pH sensor) is the same as the resistance of the resistor 422 at that point 512 in time (thus the analyte level sensed is at the reference analyte level corresponding the predetermined electrical resistance of the resistor 422). Prior to that point 512, the output voltage signal 424 is less than zero, thus indicating that the resistance of the sensing element 310 is higher than the resistance of the resistor 422, which indicates that the analyte level sensed is higher (due to higher pH than the reference pH) than the reference analyte level. After the point 512, the output voltage signal 424 is more than zero, thus indicating that the analyte level sensed is lower (due to lower pH than the reference pH) than the reference analyte level. It can also be observed that the output voltage signal 424 has a maximum range of +/−10V, which is proportional (the same in this case) to the supply voltage of the power source 432 (two 10V batteries). For example, the point 512 may be referred to as the output voltage porosity switch point which is a predetermined reference point in the measurement circuit 420. It can be appreciated that if choosing a different reference pH level, the resistance value of the resistor 422 would need to be changed accordingly based on (e.g., to match) the sensing element output to achieve the output voltage porosity switch point. Furthermore, in the example, the amount of output voltage 424 above or below the reference/predetermined voltage level (e.g., 0V as shown in FIG. 5B) corresponds to (e.g., substantially proportionally) the amount of pH above or below the reference pH level provided by the reference element 422.

Figure 6A:
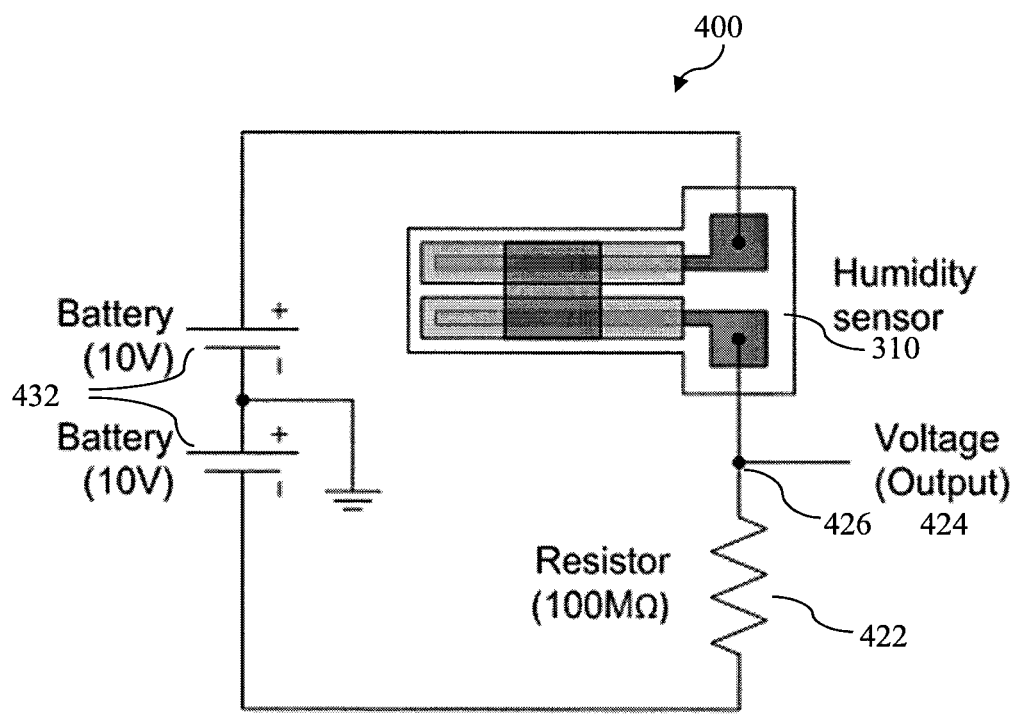
FIG. 6A depicts a schematic circuit drawing of the sensing device implemented or used as a humidity sensor device according to an example embodiment of the present invention.
Figure 6B:
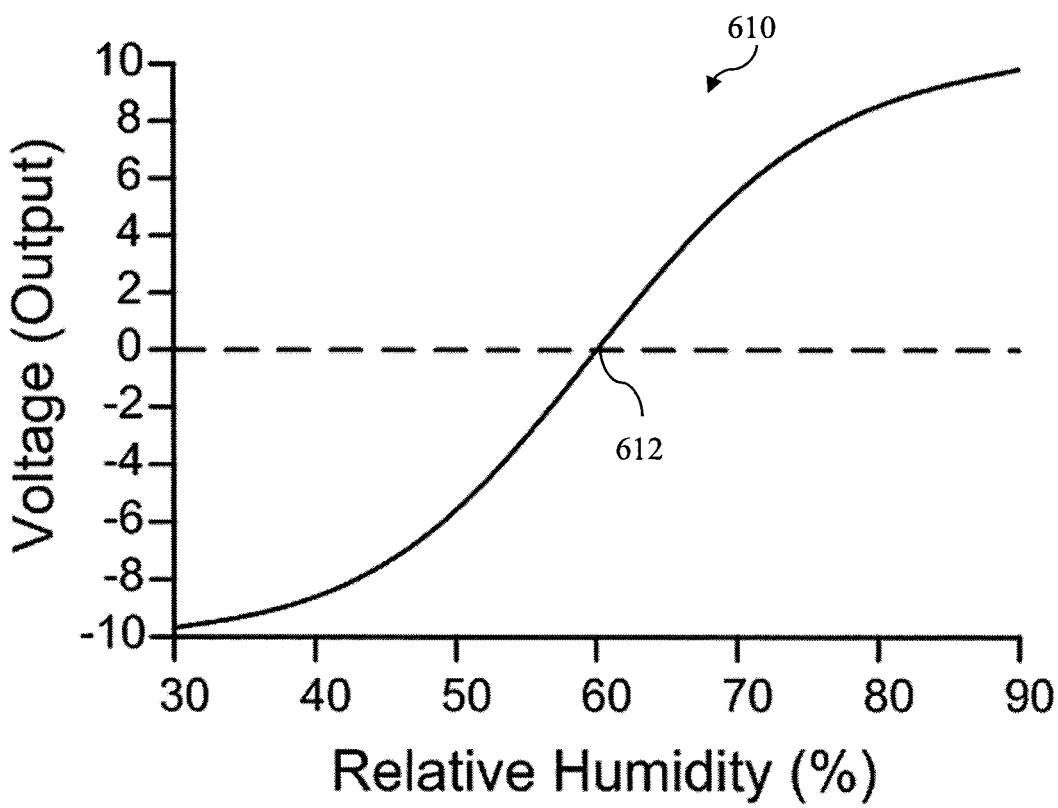
FIG. 6B depicts a plot of the output voltage signal (V) against the relative humidity (%) of the humidity sensor device of FIG. 6A.

As another example, FIG. 6A depicts a schematic circuit drawing of the sensing device 400 implemented or used as a humidity sensor device. FIG. 6B depicts a plot 610 of the output voltage signal (V) 426 against the relative humidity (%). It can be observed that as relative humidity increases, the resistance of the sensing element 310 decreases and thus increasing the output voltage signal 426 across the resistor 422. At approximately 60% relative humidity, the output voltage crosses 0V indicating that the resistance of the sensing element (being used as a humidity sensor) is the same as the resistance of the resistor 422 at that point 612 (thus the analyte level sensed is at the reference analyte level corresponding to the predetermined electrical resistance of the resistor 422). Prior to that point 612, the output voltage signal is less than 0V, thus indicating that the resistance of the sensing element 310 is higher than the resistance of the resistor 422, which in this case indicates that the analyte level sensed is less (due to lower humidity than the reference) than the reference analyte level. After that point 612, the output voltage signal 424 is more than 0V, thus in this case indicating that the analyte level sensed is higher (due to higher humidity than the reference) than the reference analyte level. It can also be observed that the output voltage signal 424 has a maximum range of +/−10V, which is proportional (in this case, the same) to the supply/driving voltage of the power source 432 (two 10V batteries). It will be appreciated by a person skilled in the art that the output voltage range changes when the supply/input/driving voltage changes. For example, the supply voltage may be determined based on various I/O voltage requirements such as a display. As an example based on a display, for bi-stable display, the driving voltage may be +/−10V, but for electrochromic display, the driving voltage may be +/−3V, and so on. In the example, the amount of output voltage 424 above or below the reference/predetermined voltage level (e.g., 0V as shown in FIG. 6B) corresponds to (e.g., substantially proportionally) the amount of relative humidity above or below the reference humidity level provided by the reference element 422.

According to various example embodiments, the measurement circuit of the sensing device may be extended to indicate a range of analyte levels by using a range of predetermined resistance values, such as a predetermined resistance value for a respective analyte level. In this regard, the sensing device may comprise one or more additional sensing elements and one or more additional reference elements, each additional sensing element configured to sense/detect the analyte and produce an electrical output which is variable based the level of the analyte sensed/detected, and each additional reference element comprising a resistor, and the electrical property of the reference element being a predetermined electrical resistance corresponding to an additional reference level of analyte for measuring the level of the analyte sensed with respect to the additional reference element.

Figure 7:
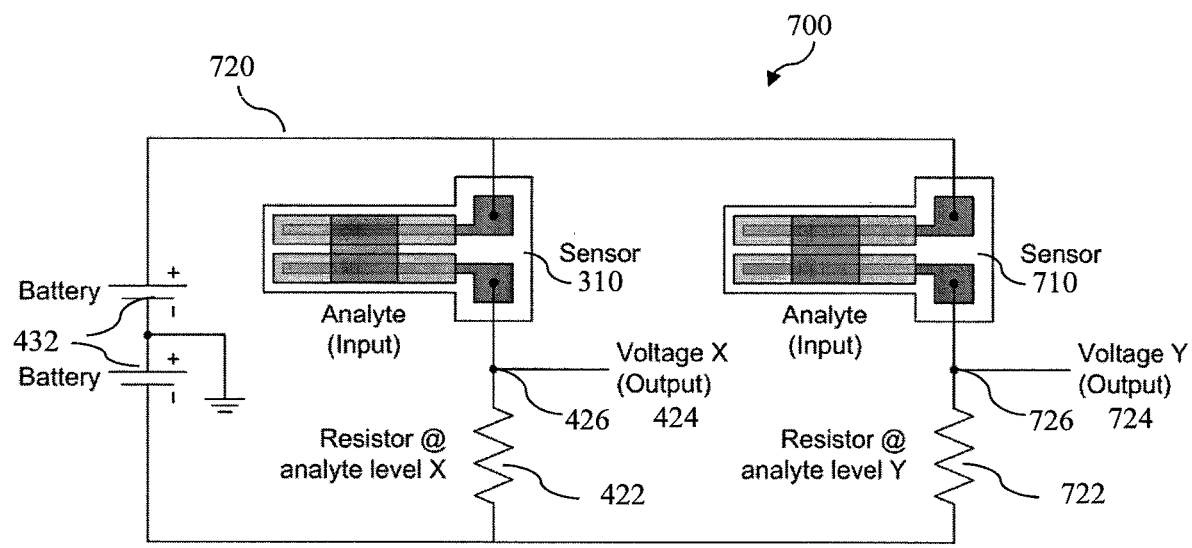
FIG. 7 depicts a schematic circuit drawing of a sensing device having a measurement circuit configured for two-level sensing of analyte level according to an example embodiment of the present invention.

By way of an example and without limitations, FIG. 7 depicts a schematic circuit drawing of a sensing device 700 having a measurement circuit 720 configured for two-level sensing of analyte level. As shown in FIG. 7, a first sensing element 310 and a first reference element 422 are connected in series for measuring the level of the analyte sensed with reference to the first reference element 422 (having a predetermined electrical resistance corresponding to a first reference level (e.g., X) of analyte for comparison with the level of analyte sensed) via the measurement output signal 424 from the output node 426. Further, a second sensing element 710 and a second reference element 722 are connected in series for measuring the level of the analyte sensed with reference to the second reference element 722 (having a predetermined electrical resistance corresponding to a second reference level (e.g., Y) of analyte for comparison with the level of analyte sensed) via the measurement output signal 724 from the output node 726. The serially connected first sensing element 310 and first reference element 422 are connected in parallel to the serially connected second sensing element 710 and second reference element 722. Accordingly, based on the measurement circuit 720 as shown in FIG. 7, the level of analyte sensed can be determined according to Table 1 below, assuming analyte level X is less than analyte level Y.

TABLE 1

| Level of Analyte Sensed based on the Two-Level Measurement Circuit 720 shown in FIG. 7 | | |
|---|---|---|
| | Voltage X | Voltage Y |
| Analyte Level < X | >0 | >0 |
| Analyte Level = X | =0 | >0 |

TABLE 1-continued

| Level of Analyte Sensed based on the Two-Level Measurement Circuit 720 shown in FIG. 7 | | |
|---|---|---|
| | Voltage X | Voltage Y |
| X < Analyte Level < Y | <0 | >0 |
| Analyte Level = Y | <0 | =0 |
| Analyte Level > Y | <0 | <0 |

It will be appreciated that the measurement circuit can be further extended/expanded to indicate additional ranges of analyte levels by incorporating additional sensing elements and reference elements having a predetermined electrical resistance. For example, for each additional analyte level, an additional sensing element and an additional reference element connected in series may be added to the measurement circuit in parallel in the same manner in which the sensing element 710 and the resistance element 722 are added. For example and without limitations, the output voltage signals 424, 724 can be used to directly drive flexible electrophoretic or electrochromic displays.

Figure 8:
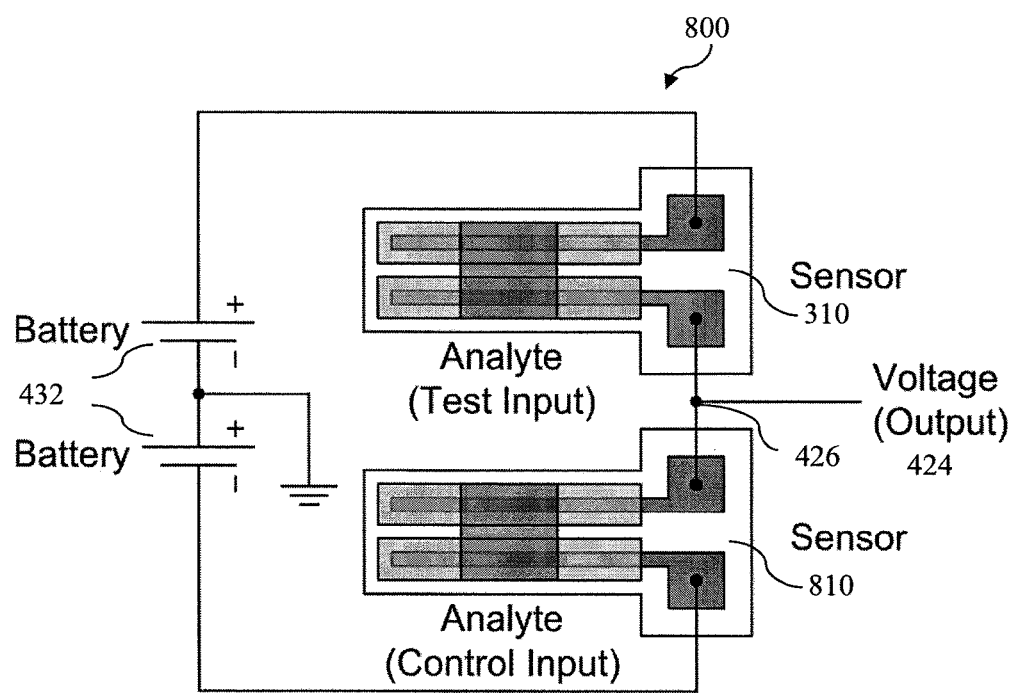
FIG. 8 depicts a schematic circuit drawing of a sensing device whereby the reference element is a second sensing element according to an example embodiment of the present invention.

In various example embodiments, the reference element 422 may be a second sensing element configured to sense the analyte or another analyte and produce an electrical output which is variable based the level of the analyte or the another analyte sensed. By way of example only and without limitation, this may be applicable in circumstances where there is a need to relate analyte levels. FIG. 8 depicts a schematic circuit drawing of a sensing device 800 whereby the reference element is a second sensing element 810. As an example, for applications that require both control/reference and test sensing, the first sensing element 310 may serve as a test sensor and the second sensing element 810 may serve as a control or reference sensor. By way of an example only, the second sensing element 810 may be exposed to a certain/predetermined reference pH level (e.g., pH 7). Therefore, if the first sensing element 310 also senses the same pH level as the reference pH level, the output voltage 724 would be 0V. Otherwise, the output voltage voltage 724 not be 0V. In such a configuration, the test and control/reference sensors 310, 810 can be seamlessly integrated and the output voltage signal 424 will indicate the difference in analyte levels between the test and control/reference sensors 310, 810 by subtracting any common-mode changes, e.g., which advantageously cancels out the environmental effects. As a further example, in applications that require accuracy over an extended period of time, the test and control/reference sensors 310, 810 may again be utilized to subtract any common-mode environment/material-related electrical behavior drifts.

According to various example embodiments, the measurement circuit of the sensing device is further configured to incorporate a differential amplifier to provide additional amplification/gain to the measurement output signal. This would advantageously improve the response time of sensing device. By way of examples and without limitations, FIG. 9 depicts a schematic circuit drawing of a sensing device 900 whereby the measurement circuit is configured to incorporate a passive differential amplifier, and FIG. 10 depicts a schematic circuit drawing of a sensing device 1000 whereby the measurement circuit is configured to incorporate an active differential amplifier.

Figure 9:
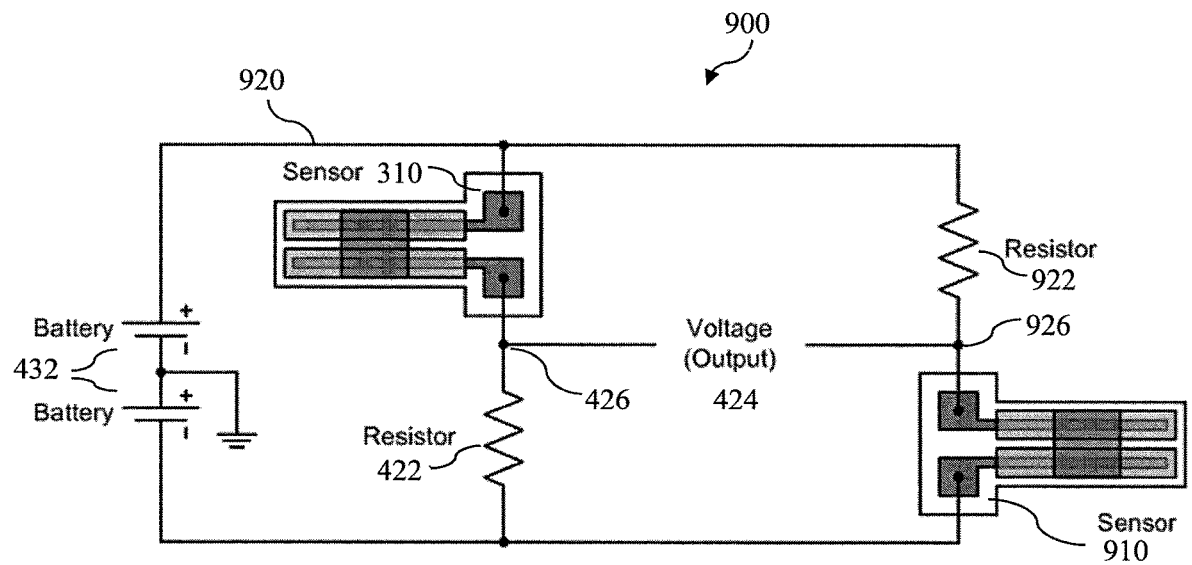
FIG. 9 depicts a schematic circuit drawing of a sensing device whereby the measurement circuit is configured to incorporate a passive differential amplifier according to an example embodiment of the present invention.

As shown in FIG. 9, the measurement circuit 900 comprises two sensing elements 310, 910 operating as a differential pair, and the output voltage 424 is connected between two sensing elements 310, 910. The sensing element 310 is connected in series with the reference element 422, with an output node 426 located therebetween. The reference element 922 is connected in series with the sensing element 910 (in an opposite arrangement to the sensing element 310 and the reference element 422), with an output node 926 located therebetween. As the resistance of both of the sensing elements 310, 910 change, the output voltage 424 across the output nodes 426, 926 changes in different directions thereby translating to higher gain.

Figure 10:
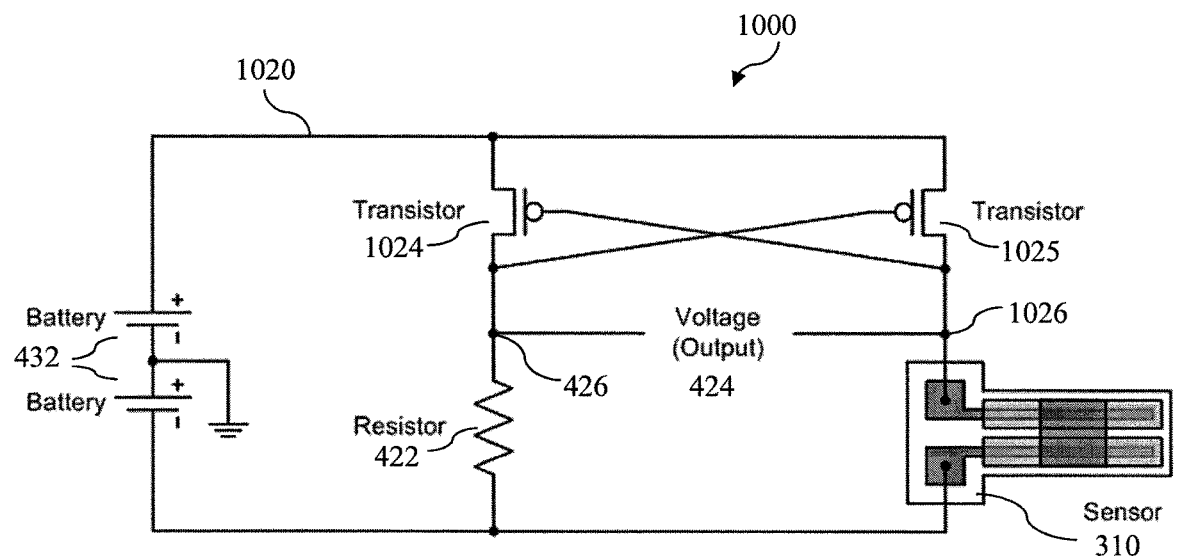
FIG. 10 depicts a schematic circuit drawing of a sensing device whereby the measurement circuit is configured to incorporate an active differential amplifier according to an example embodiment of the present invention.

As shown in FIG. 10, the measurement circuit 1000 comprises two cross-coupled transistors 1024, 1025 connected to the sensing element 310 and the reference element 422. The sensing element 310 is connected in series with the transistor 1025, with an output node 1026 located therebetween. The transistor 1024 is connected in series with the reference element 422, with an output node 426 located therebetween. The cross-coupled transistors 1024 operate as a positive feedback, amplifying the voltage differences across the output nodes 426, 1026 based on the sensing element 310 and the reference element 422.

Figure 11:
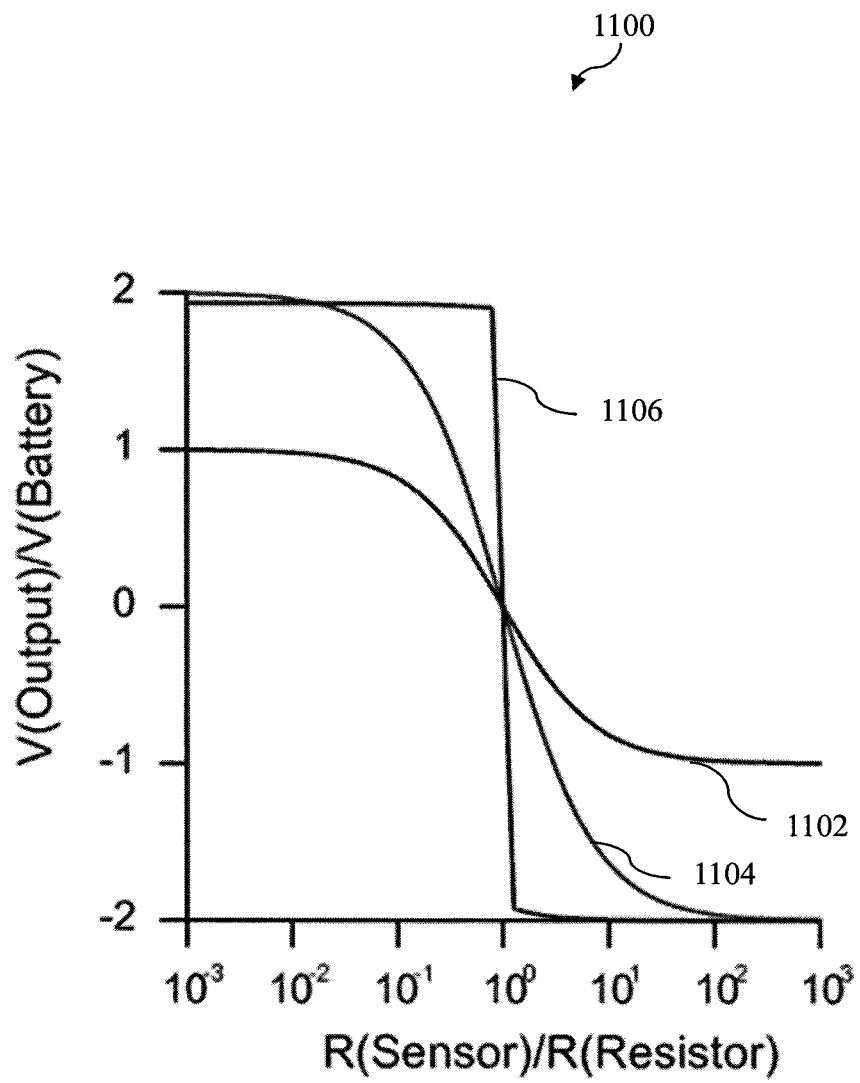
FIG. 11 depicts plots comparing the gains (output voltage/supply voltage) of different measurement circuit configurations against the difference/ratio between the electrical resistance of the sensing element and the reference element (R(sensing element)/R(reference element))
Figure 12A:
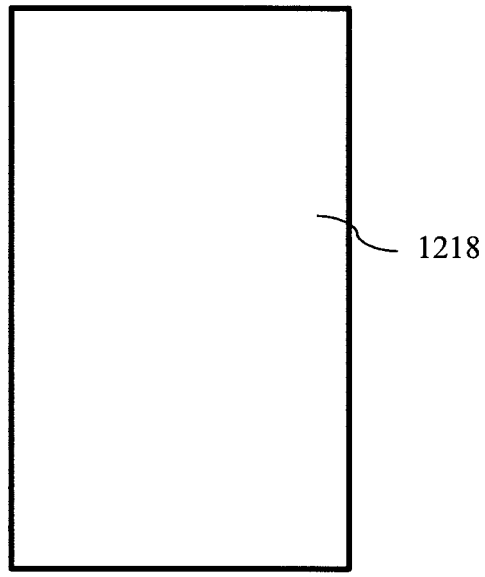
FIGS. 12A to 12D depict a schematic illustration of an exemplary method of fabricating the sensing element according to various example embodiment of the present invention.
Figure 12B:
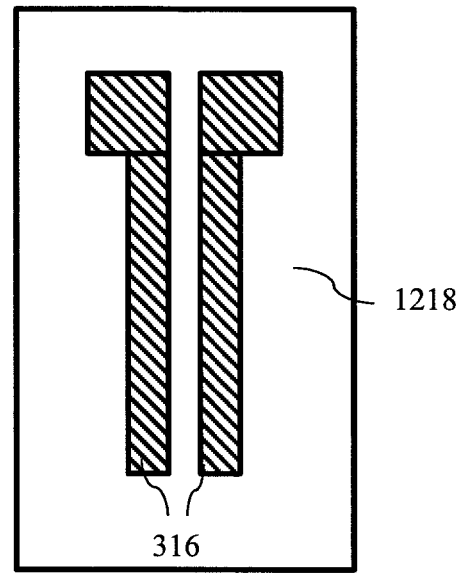
Figure 12C:
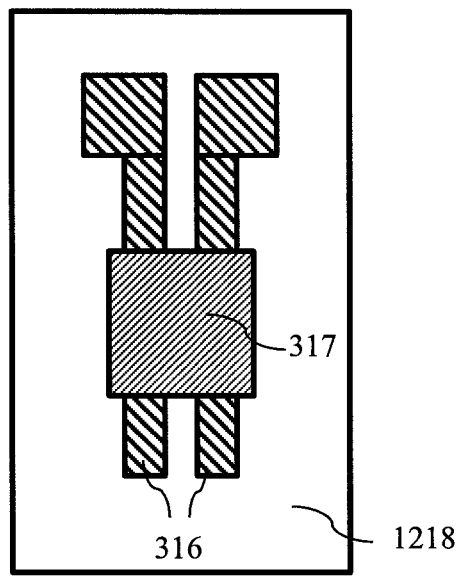
Figure 12D:
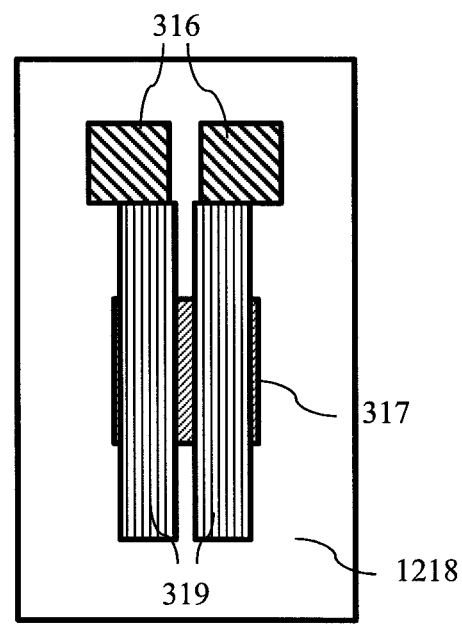

FIG. 11 depicts plots 1100 comparing the gains (output voltage/supply voltage) of different measurement circuit configurations against the difference/ratio between the electrical resistance of the sensing element and the reference element (R(sensing element)/R(reference element)), namely, for the measurement circuit configurations as shown in FIG. 4 (no additional amplification) 1102, FIG. 9 (with passive differential amplifier) 1104, and FIG. 10 (with active differential amplifier) 1106. From FIG. 11, it can be observed that the measurement circuit 420 of FIG. 4 does not provide additional amplification and has a unity gain with respect to the power source, which is the lowest amongst the three configurations being compared. It can also be observed that the maximum range of the output voltage signal is limited to the supply voltage of the power source. Nevertheless, the measurement circuit 420 is the simplest amongst the three configurations with four components (a sensing element, a reference element and two batteries). The measurement circuit 900 as shown in FIG. 9 comprises two sensing elements 310, 910 operating as a differential pair. As the resistance/conductivity of the two sensing elements 310, 910 change, the voltage across the output changes in different directions thereby translating to higher gain. With six components, the measurement circuit 900 has improved amplification and the maximum range of the output voltage signal is twice the supply voltage of the power source as shown in FIG. 11. The measurement circuit 1000 comprises two cross-coupled transistors 1024 connected to the sensing element 310 and reference element 422. As the cross-coupled transistors operate as a positive feedback and amplifies the small voltage differences across the output caused by the sensing element 310, the gain of the measurement circuit 1020 is high and is a function of the gain of the cross-coupled transistors 1024. With six components (including two transistors 1024), the measurement circuit 1020 has high gain and the maximum range of the output voltage signal is twice the supply voltage of the power source as shown in FIG. 11. It will be appreciated to a person skilled in the art that the amplification of the measurement circuit 1000 is dependent on the on/off ratio of the transistors 1024/1025 since the differential amplifier operates by switching the transistors 1024/1025 on/off. Furthermore, the transistors 1024/1025 possess a non-linear effect depending on transconductance.

By way of an example for illustration purposes only, an exemplary method of fabricating the sensing element 310 will now be described with reference to FIGS. 12A to 12D according to various example embodiment of the present invention. As a first step shown in FIG. 6A, a substrate 1218 is provided upon which the sensing element 310 and the measurement circuit 420 may be formed (preferably, printed). It will be appreciated that the substrate 1218 may be made of any materials as desired/appropriate for the desired application, such as paper, plastic, and so on. It will also be appreciated that the thickness of the substrate 1218 may be chosen/determined as appropriate to provide mechanical support for the sensing element 310 and the measurement circuit 420 to be formed thereon. Thereafter, as shown in FIG. 6B, a conductive member (electrodes) 316 is disposed (preferably, printed) on the substrate 1218. The conductive member 316 may be made of any materials as desired/appropriate for the desired application such as Ag, AgCl, Cu and so on. Subsequently, as shown in FIG. 6C, a sensing material 317 is disposed (preferably, printed) over a portion of the conductive member 316 so as to encapsulate the portion of the conductive member 316 (cross-sectionally) on the substrate 318. As mentioned hereinbefore, it will be appreciated to a person skilled in the art that specific sensing materials may be selected for detecting/sensing specific analytes for various sensing applications, and for example, the sensing material 317 may be made of PVDF, PANI, ZnO, and so on. Subsequently, an insulating layer 319 is disposed (preferably printed) over and along each of the electrodes 316, including over portions of the sensing material 317 above the respective electrodes 316 so as to encapsulate the electrodes from being exposed to the analyte 312. It will be appreciated that the insulating layer 319 may be made of any suitable materials such as polymer, epoxy, and so on. Subsequently (or before or simultaneously with forming the sensing element 310), the measurement circuit 420 (not shown in FIGS. 6A to 6D) is formed (preferably, printed) on the substrate 1218 thereby producing a sensing device as an integrated circuit. It will be appreciated that the present invention is not limited to any specific dimensions of various components of the sensing device formed on the substrate 1218, and suitable dimensions may be selected/determined as appropriate for the desired application(s). Printing may also be achieved by various techniques known in the art, such as, but not limited to, inkjet, screen, gravure, flexographic, offset, pad printing, and so on.

Figure 13:
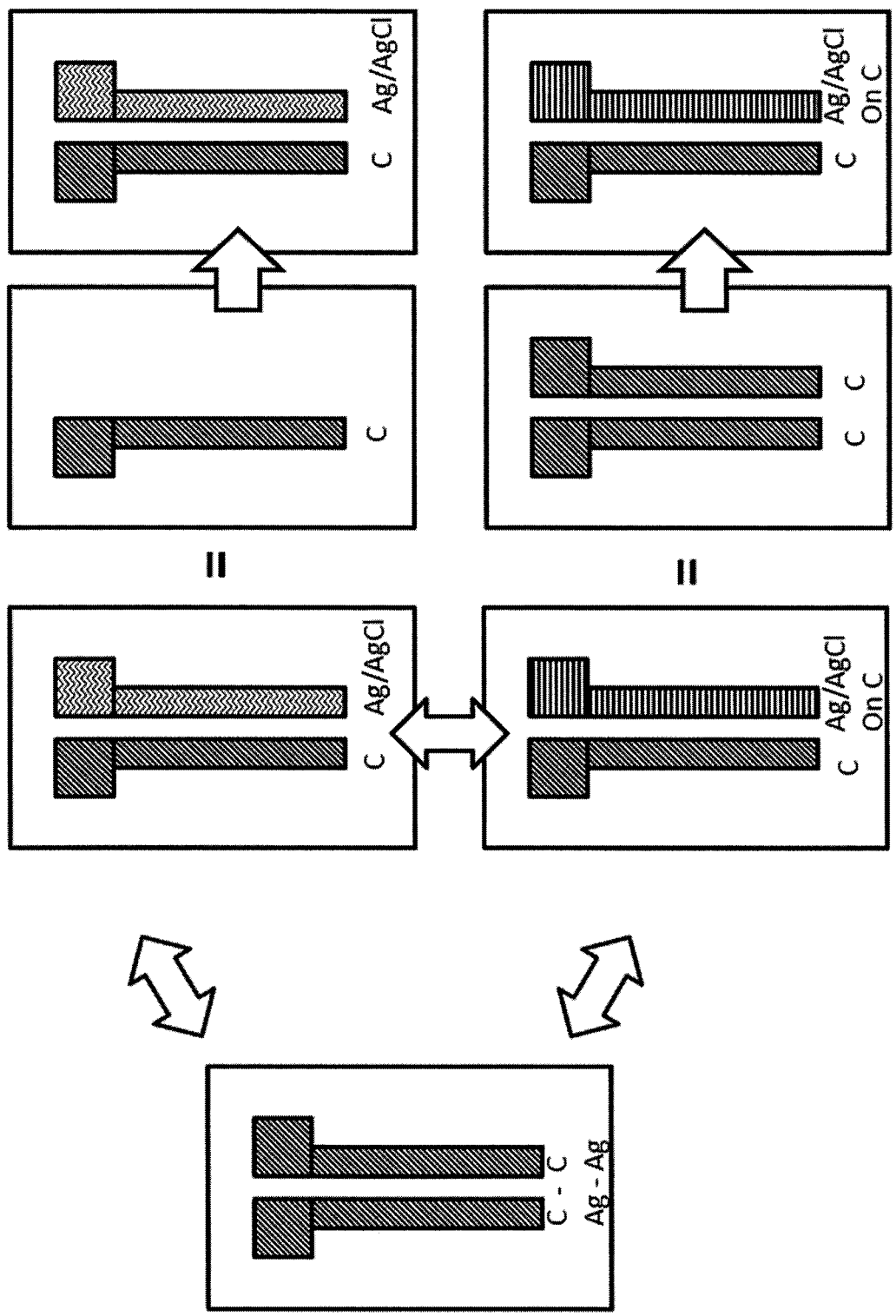
FIG. 13 depicts a schematic drawing illustrating that the two electrodes of the sensing element can be made of the same or different materials according to various embodiments of the present invention.

FIG. 13 depicts a schematic drawing illustrating that the two electrodes 316 of the sensing element 310 may be made of the same or different materials according to various embodiments of the present invention. For example only, in the case of the same materials, the first and second electrodes may each be made of C (carbon) or Ag (silver). For example only, in the case of different materials, a first electrode may be made of C and a second electrode may be made of Ag/AgCl. As another example, a first electrode may be made of C (carbon) and a second electrode may be made of Ag/AgCl on C.

Accordingly, various embodiments of the present invention advantageously provide a sensing device having an integrated circuit comprising the sensing element and the measurement circuit for signal measurement/acquisition on one substrate. This advantageously avoids the need for a relatively expensive and separate back-end signal measurement device required in conventional electronic sensors due to low-voltage measurement requirements, thereby significantly reducing costs and complexity and enabling low-cost applications. Furthermore, for example due to the above integration, the sensing device may be realized as printed electronics, thereby significantly expanding the range of applications.

For example, printed circuits for electrical signal differentiation, amplification and computation using printed electronics may be provided, thereby providing low-cost signal diagnostic systems for information gathering, processing, and transmission. For example and without limitations, the sensing device may be applied to sense/detect analytes from various mediums/sensing sources (including a combination thereof), such as environmental changes (e.g., temperature, humidity, etc.), chemical species (e.g., solid, liquid or gas), and biological triggers (e.g., pH, etc.). In various embodiments, there is provided circuits for diagnostic systems comprises a printed sensing element, printed measurement circuit, and display using one or more layers and one or more elements. Various embodiments of the present invention are based on translating source levels to an electrical property (in particular, electrical conductivity) by means of circuit configurations, integrating the sensing element (sensor) into the circuit that amplifies/compares electrical signals proportional to source/analyte levels, and a display to indicate the source/analyte levels.

Based on various embodiments described hereinbefore, a printed sensor circuit may be provided for various applications such as both sensing and signal amplification, to offset errors due to sensing material's instability, to integrate both control and test sensing, and to any material that is sensitive to environment changes, e.g., temperature, moisture, chemical (solid, liquid or gas), pH, and so on. It will be appreciated that the sensing device described herein may be adapted or implemented as other devices, such as printed field-effect transistor (FET), chemical field-effect transistor (ChemFET), ion-sensitive field-effect transistor (ISFET), and so on.

While embodiments of the present invention have been particularly shown and described with reference to specific embodiments, it should be understood by those skilled in the art that various changes in form and detail may be made therein without departing from the scope of the present invention as defined by the appended claims. The scope of the present invention is thus indicated by the appended claims and all changes which come within the meaning and range of equivalency of the claims are therefore intended to be embraced.

What is claimed is:

1. A sensing device for measuring a level of an analyte, the sensing device comprising:
a sensing element configured to sense the analyte and produce an electrical output which is variable based on the level of the analyte sensed;
a measurement circuit comprising a reference element for providing an electrical property, the measurement circuit being connected to the sensing element and configured to provide a measurement output signal based on the electrical property of the reference element and the electrical output of the sensing element; and
a power source for providing a supply voltage to the sensing element and the reference element, the power source comprising a first power source and a second power source connected in series, wherein
the sensing element and the reference element are connected in series, and the measurement output signal is output from an output node located between the sensing element and the reference element,
the sensing element is connected to the power source such that the sensing element is connected between a first terminal of the power source and the output node,
the reference element is connected to the power source such that the reference element is connected between a second terminal of the power source and the output node,
the measurement output signal indicates the level of the analyte sensed with respect to the electrical property of the reference element and is an output voltage signal, and
the measurement circuit is configured to apply a ground to a node located in between the first and second power sources connected in series.

2. The sensing device according to claim 1, wherein the measurement circuit is configured such that a maximum range of the output voltage signal is proportional to the supply voltage of the power source.

3. The sensing device according to claim 2, wherein the maximum range of the output voltage signal is substantially the same as the supply voltage or proportionally greater than the supply voltage.

4. The sensing device according to claim 1, wherein the sensing element comprises a conductive member and a sensing material disposed on the conductive member for receiving the analyte, the sensing material having an electrical property which is variable based on the level of the analyte received, thereby causing the electrical output of the sensing element at the conductive member to be variable based on the level of the analyte sensed.

5. The sensing device according to claim 4, wherein the conductive member comprises a plurality of spaced apart electrodes, the sensing material being disposed on the plurality of spaced apart electrodes so as to provide an electrical connection between the spaced apart electrodes via the sensing material.

6. The sensing device according to claim 4, wherein the electrical property is an electrical conductivity of the sensing material, and the electrical output of the sensing element at the conductive member corresponds to the electrical conductivity of the sensing material.

7. The sensing device according to claim 1, wherein the sensing element and the measurement circuit are integrally formed on a substrate.

8. The sensing device according to claim 7, wherein the sensing element and the measurement circuit are printed on the substrate.

9. The sensing device according to claim 1, wherein the reference element comprises a resistor, and the electrical property of the reference element is a predetermined electrical resistance corresponding to a reference level of the analyte such that the measurement output signal indicates the level of the analyte sensed with respect to the reference level of the analyte based on the electrical output of the sensing element with respect to the predetermined electrical resistance of the reference element.

10. The sensing device according to claim 9, further comprising one or more additional sensing elements and one or more additional reference elements, each additional sensing element configured to sense the analyte and produce an electrical output which is variable based the level of the analyte sensed, and each additional reference element comprising a resistor, and the electrical property of the reference element is a predetermined electrical resistance corresponding to an additional reference level of the analyte for measuring the level of the analyte sensed with respect to the predetermined electrical resistance of the additional reference element.

11. The sensing device according to claim 1, wherein the reference element is a second sensing element, the second sensing element configured to sense the analyte or another analyte and produce an electrical output which is variable based the level of the analyte or said another analyte sensed.

12. The sensing device according to claim 1, wherein the measurement circuit is further configured to incorporate a differential amplifier to provide additional amplification to the measurement output signal.

13. A method of fabricating a sensing device for measuring a level of an analyte, the method comprising:
  forming a sensing element configured to sense the analyte and produce an electrical output which is variable based on the level of the analyte sensed;
  forming a measurement circuit comprising a reference element for providing an electrical property, the measurement circuit being connected to the sensing element and configured to provide a measurement output signal based on the electrical property of the reference element and the electrical output of the sensing element; and
  providing a power source for providing a supply voltage to the sensing element and the reference element, the power source comprising a first power source and a second power source connected in series, wherein
  the sensing element and the reference element are connected in series, and the measurement output signal is output from an output node located between the sensing element and the reference element,
  the sensing element is connected to the power source such that the sensing element is connected between a first terminal of the power source and the output node,
  the reference element is connected to the power source such that the reference element is connected between a second terminal of the power source and the output node,
  the measurement output signal indicates the level of the analyte sensed with respect to the electrical property of the reference element and is an output voltage signal, and
  the measurement circuit is configured to apply a ground to a node located in between the first and second power sources connected in series.

14. The method according to claim 13, wherein the measurement circuit is configured such that a maximum range of the output voltage signal is proportional to the supply voltage of the power source.

15. The method according to claim 13, wherein forming a sensing element comprises forming a conductive member and forming a sensing material disposed on the conductive member for receiving the analyte, the sensing material having an electrical property which is variable based on the level of the analyte received, thereby causing the electrical output of the sensing element at the conductive member to be variable based on the level of the analyte sensed.

16. The method according to claim 15, wherein the electrical property is an electrical conductivity of the sensing material, and the electrical output of the sensing element at the conductive member corresponds to the electrical conductivity of the sensing material.

17. The method according to claim 13, wherein the sensing element and the measurement circuit are integrally formed on a substrate.

18. The method according to claim 17, wherein the sensing element and the measurement circuit are printed on the substrate.

* * * * *